United States Patent [19]
Eberhard et al.

[11] Patent Number: 5,187,659
[45] Date of Patent: Feb. 16, 1993

[54] CONE BEAM SCANNING TRAJECTORIES FOR THREE-DIMENSIONAL COMPUTERIZED TOMOGRAPHY DATA ACQUISITION WHERE OBJECT IS LARGER THAN THE FIELD OF VIEW

[75] Inventors: Jeffrey W. Eberhard; Kwok C. Tam, both of Schenectady, N.Y.

[73] Assignee: General Electric Company, Schenectady, N.Y.

[21] Appl. No.: 577,163

[22] Filed: Sep. 4, 1990

[51] Int. Cl.$^5$ ............................................. G06F 15/42
[52] U.S. Cl. ................................................. 364/413.15
[58] Field of Search .................... 364/413.13, 413.15

[56] References Cited

PUBLICATIONS

"The Dynamic Spatial Reconstructor", R. A. Robb et al., J. Med. Syst., vol. 4, No. 2, pp. 253-288 (1980).
"Iterative Three-Dimensional Reconstruction from Twin-Cone Beam Projections", M. Schlindwein, IEEE Trans. Nucl. Sci., vol. NS-25, No. 5, pp. 1135-1143 (Oct. 1978).
"Convolutional Reconstruction from Cone-Beam Projection Data", G. N. Minerbo, IEEE Trans. Nucl. Sci., vol. NS-26, No. 2, pp. 2682-2684 (Apr. 1979).
"An Inversion Formula for Cone-Beam Reconstruction", H. K. Tuy, SIAM J. Math., vol. 43, No. 3, pp. 546-552 (Jun. 1983).
"Practical Cone-Beam Algorithm", L. A. Feldkamp et al., J. Opt. Soc. Am. A., vol. 1, No. 6, pp. 612-619 (Jun. 1984).
"Image Reconstruction from Cone-Beam Projections: Necessary and Sufficient Conditions and Reconstruction Methods", B. D. Smith, IEEE Trans. Med. Imag., vol. MI-44, pp. 14-25 (Mar. 1985).
"Quantitative Cone-Beam Construction", H. Hu et al., SPIE Medical Imaging III: Image Processing, vol. 1092, pp. 492-501 (1989).

*Primary Examiner*—Gail O. Hayes
*Attorney, Agent, or Firm*—Paul R. Webb, II

[57] ABSTRACT

A configuration for three-dimensional cone beam computerized tomography imaging which minimizes the incompleteness of the data set and, at the same time, avoids corrupted data and resulting artifacts when only a portion of an object is imaged, the object being of greater axial extent compared to a cylindrical field of view. At least two circular source scanning trajectories are defined centered on a rotation axis and lying respectively in two endplanes defining the axial extent of the field of view. At least one cone beam x-ray source and at least one corresponding two-dimensional array detector are employed to scan the object along the source scanning trajectories, while acquiring cone beam projection data only from rays passing through the field of view. Preferably, at least one additional circular source scanning trajectory is defined, centered on the rotation axis and lying in a plane intermediate the two endplanes.

11 Claims, 9 Drawing Sheets

$R(x_0, y_0, z_0) = \iint_{\text{plane}} f(x,y,z)\, da$

CONE BEAM SCANNING TRAJECTORIES FOR THREE-DIMENSIONAL COMPUTERIZED TOMOGRAPHY DATA ACQUISITION WHERE OBJECT IS LARGER THAN THE FIELD OF VIEW

BACKGROUND OF THE INVENTION

The present invention relates generally to three-dimensional (3D) computerized tomography (CT) and, more particularly, to methods and systems for minimizing the amount of missing data and, at the same time, avoiding corrupted data and resulting artifacts in image reconstruction when a cone beam configuration is used to image a portion of an object which is larger than the field of view.

In conventional computerized tomography for both medical and industrial applications, an x-ray fan beam and a linear array detector are employed. Two-dimensional (2D) imaging is achieved. While the data set is complete and image quality is correspondingly high, only a single slice of an object is imaged at a time. When a 3D image is required, a "stack of slices" approach is employed. Acquiring a 3D data set one 2D slice at a time is inherently slow. Moreover, in medical applications, motion artifacts occur because adjacent slices are not imaged simultaneously. Also, dose utilization is less than optimal, because the distance between slices is typically less than the x-ray collimator aperture, resulting in double exposure to many parts of the body.

One approach to acquiring a 3D data set simultaneously is described in the literature: Richard A. Robb, Arnold H. Lent, Barry K. Gilbert, and Aloysius Chu, "The Dynamic Spatial Reconstructor", J. Med. Syst., Vol. 4, No. 2, pp. 253-288 (1980). The Dynamic Spatial Reconstructor employs twenty-eight x-ray sources and twenty-eight x-ray imaging systems in a synchronous scanning system to acquire data for a conventional "stack of slices" reconstruction all at once. The actual geometry is a stack of twenty-eight cone beams scanning twenty-eight respective cylindrical volumes, with area detectors employed to acquire 240 adjacent video lines of data for each slice. However, the data is analyzed as though it is from a stack of fan beam projections, stacked in an axial direction, using conventional 2D reconstruction algorithms. Consistent with this approach, in the Dynamic Spatial Reconstructor the divergence of the x-ray beam above and below the central slice of each cylindrical volume is only ±4°.

In a system employing true cone beam geometry, a cone beam x-ray source and a 2D area detector are employed. An object is scanned, preferably over a 360° angular range, either by moving the x-ray source in a scanning circle around the object, while keeping the 2D area detector fixed with reference to the source, or by rotating the object while the source and detector remain stationary. In either case, it is relative movement between the source and object which effects scanning. Compared to the conventional 2D "stack of slices" approach to achieve 3D imaging the cone beam geometry has the potential to achieve rapid 3D imaging of both medical and industrial objects, with improved dose utilization.

The cone beam geometry for 3D imaging has been discussed extensively in the literature, as represented by the following: M. Schlindwein, "Interactive three-Dimensional Reconstruction from Twin-Cone Beam Projections", IEEE Trans. Nucl.Sci., Vol. NS-25, No. 5, pp. 1135-1143 (October 1978); Gerald N. Minerbo, "Convolutional Reconstruction from Cone-Beam Projection Data", IEEE Trans. Nucl. Sci., Vol. NS-26, No. 2, pp. 2682-2684 (April 1979); Heang K. Tuy, "An Inversion Formula for Cone-Beam Reconstruction", SIAM J. Math., Vol. 43, No. 3, pp. 546-552 (June 1983); L. A. Feldkamp, L. C. Davis, and J. W. Kress, "Practical Cone-Beam Algorithm", J. Opt. Soc. Am. A., Vol. 1, No. 6, pp. 612-619 (June 1984); Bruce D. Smith, "Image Reconstruction from Cone-Beam Projections: Necessary and Sufficient Conditions and Reconstruction Methods", IEEE Trans. Med. Imag., Vol. MI-44, pp. 14-25 (March 1985); and Hui Hu, Robert A. Kruger, and Grant T. Gullberg, "Quantitative Cone-Beam Construction", SPIE Medical Imaging III: Image Processing, Vol. 1092, pp. 492-501 (1989).

Figure 1:
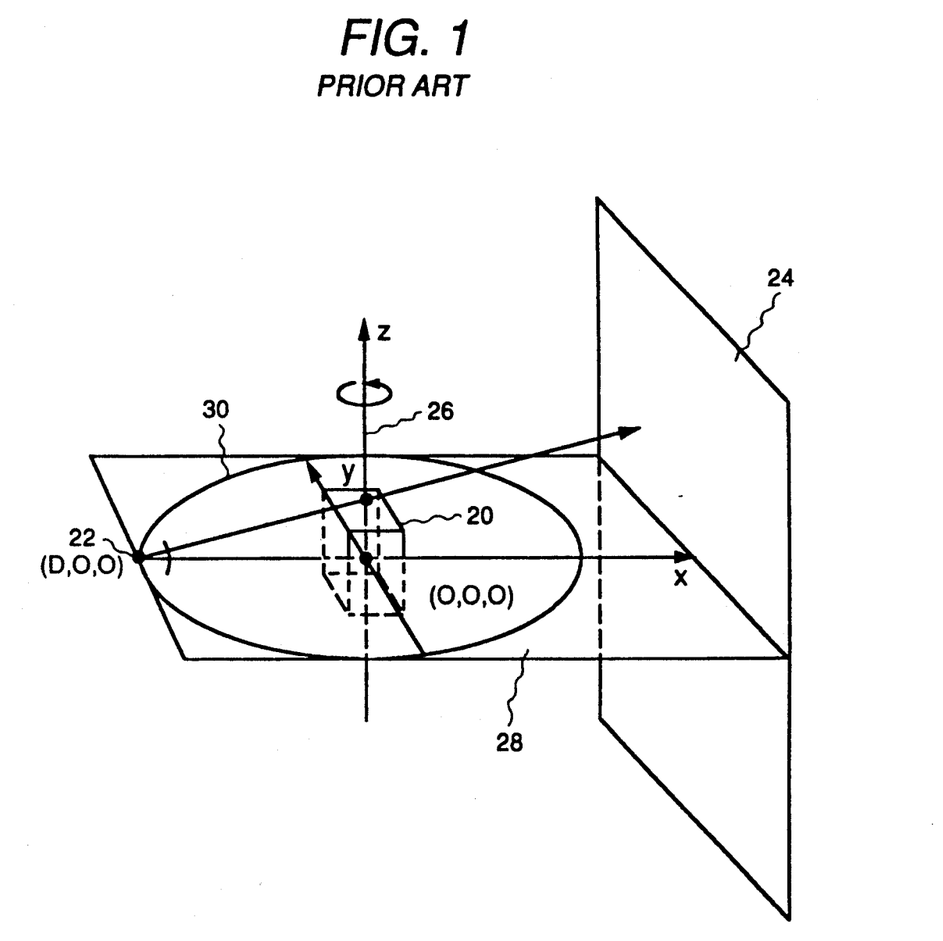
FIG. 1, referred to hereinabove, represents conventional cone beam scanning geometry for 3D CT.

A typical scanning and data acquisition configuration employing cone-beam geometry is depicted in FIG. 1. An object 20 is positioned within a field of view between a cone beam x-ray point source 22 and a 2D detector array 24, which provides cone beam projection data. An axis of rotation 26 passes through the field of view and object 20. For purposes of analysis, a midplane 28 is defined which contains the x-ray point source 22 and is perpendicular to the axis of rotation 26. By convention, the axis of rotation 26 is referred to as the z-axis, and the intersection of the axis of rotation 26 and the midplane 28 is taken as the origin of coordinates. x and y axes lie in the midplane 28 as indicated, and the (x,y,z) coordinate system rotates with the source 22 and detector 24. For scanning the object 20 at a plurality of angular positions, the source 22 moves relative to the object 20 and the field of view along a circular scanning trajectory 30 lying in the midplane 28, while the detector 24 remains fixed with respect to the source 22.

Thus, in the configuration of FIG. 1, data are acquired at a number of angular positions around the object by scanning the source and detector along the single circular scanning trajectory 30 (or equivalently rotating the object while the source and detector remain stationary).

However, there are two limitations of the prior art single circular scanning trajectory approach which are addressed by the present invention. The first limitation is that the data set acquired is incomplete for 3D image reconstruction. The second limitation occurs when the field of view to be imaged is smaller than the entire object, a common situation in both industrial and medical applications. In this situation, some measured projections contain information from both the field of view of interest and from other regions of the object outside the field of view. The image of the field of view of interest is therefore corrupted by data resulting from overlying material.

Regarding the incomplete data set limitation, Smith, 1985, above, has shown that a cone beam data set is complete if there is a point from the x-ray source scanning trajectory on each plane passing through the object of interest (with the assumptions that the detector is locked in position relative to the source and large enough to span the object under inspection). A configuration suggested by Minerbo (1979, above) and Tuy (1983, above), which Smith points out satisfies his condition for data completeness, is to employ two circular source scanning trajectories which are perpendicular to each other. Such a scanning configuration is however difficult to implement as a practical matter. Moreover,

3 it presumes that the object fits within the scanning trajectories, and does not address the situation where an object is larger than the field of view.

SUMMARY OF THE INVENTION

Accordingly, it is an object of the invention to provide a configuration for cone beam 3D CT imaging which both eliminates the problem of contributions to projections from regions outside the field of view, and minimizes the incompleteness of the data set to the point where very high quality images can be achieved.

It is another object of the invention to provide methods and systems for fast data acquisition to minimize motion artifacts, particularly in medical imaging applications.

These and other objects are achieved by the present invention, which is applicable to scanning and data acquisition for three-dimensional computerized tomography (CT) imaging of a portion of an object within a cylindrical field of view radially centered on a rotation axis and having an axial extent defined by two endplanes perpendicular to the rotation axis, where the object is of greater axial extent than the field of view.

Briefly, a method in accordance with the invention includes the steps of defining at least two circular source scanning trajectories centered on the rotation axis and lying respectively in the two endplanes, and employing at least one cone beam x-ray source and at least one corresponding two-dimensional array detector positioned with reference to the source and with reference to the field of view to scan the object at a plurality of relative angular positions along the source scanning trajectories to acquire cone beam projection data, while acquiring data only from rays passing through the field of view.

Preferably, at least one additional circular source scanning trajectory is defined, centered on the rotation axis and lying in a plane intermediate the two endplanes. The method then includes the step of scanning the object at a plurality of angular positions along the additional source scanning trajectory to acquire cone beam projection data from rays passing through the field of view.

Thus, in accordance with the invention, only data from the field of view is acquired. In any individual scan, this results in less available data (more missing data) than would be achieved if the scan were not limited to data from only the field of view. However, when several scans are combined, the resulting available data set is larger than would be achieved in any single scan of the object, and the problem of overlying material is completely avoided. The number of source scanning trajectories chosen is a tradeoff of mechanical complexity, scanning time, and the amount of missing data that can be tolerated in a specific imaging application.

In a more particular aspect, the method includes providing at least two scan heads corresponding to the two source scanning trajectories, each scan head including a cone beam x-ray source and a two-dimensional array detector positioned with reference to the x-ray source of the particular scan head and field of view for obtaining cone beam projection data, and employing the two scan heads to simultaneously scan the object along the two source scanning trajectories.

Where at least one additional circular source scanning trajectory has been defined, the method further includes providing a separate scan head corresponding to each of the source scanning trajectories, each of the scan heads then including a cone beam x-ray source and a two-dimensional array detector positioned with reference to the x-ray source of the particular scan head in the field of view for obtaining cone beam projection data, and employing all the scan heads to simultaneously scan the object along the source scanning trajectories.

The additional source scanning trajectory may be located in a plane where it is desired to obtain exact two-dimensional computerized tomography data.

In accordance with another aspect of the invention, a system is provided which includes at least one cone beam xray source and at least one two-dimensional array detector corresponding to the source and positioned with reference to the source and the field of view for obtaining cone beam projection data from rays passing through the field of view. The system additionally includes a scanning element for effecting relative motion between the source and the object, the source moving relative to the object along at least two circular source scanning trajectories centered on the rotation axis and lying respectively in the two endplanes, so as to acquire cone beam projection data only from rays passing through the field of view with the source at a plurality of angular positions on the source scanning trajectories. Preferably, the scanning element effects relative motion between the source and the object along an additional circular source scanning trajectory centered on the rotation axis and lying in a plane intermediate the two endplanes.

In accordance with another aspect of the invention, a system includes a pair of cone beam x-ray sources and a pair of two-dimensional array detectors respectively corresponding to the sources and positioned with reference to the sources and the field of view for obtaining cone beam projection data from x-rays passing through the field of view. The system additionally includes a scanning element for effecting relative motion between the sources and the object, the sources moving relative to the object along a corresponding pair of circular source scanning trajectories entered on the rotation axis and lying respectively in the two endplanes, so as to acquire cone beam projection data only from rays passing through the field of view with the sources at a plurality of angular positions on the source scanning trajectories.

Preferably, the system includes at least one additional cone beam x-ray source and at least one additional two-dimensional array detector corresponding to the additional source and positioned with reference to the additional source of obtaining cone beam projection data from rays passing through the field of view. The scanning element also effects relative motion between the additional source and the object, the additional source moving relative to the object along an additional circular source scanning trajectory centered on the rotation axis and lying in a plane intermediate the two endplanes.

In those embodiments of the invention where a plurality of scan heads are employed to simultaneously scan the object along a plurality of source scanning trajectories, the cone beam x-ray sources of the scan heads are angularly offset so as to reduce interference caused by x-rays from one source interacting with the detector corresponding to the other source.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

DETAILED DESCRIPTION

Since the present invention is in part directed to reducing the data set incompleteness in the prior art cone beam scanning geometry of FIG. 1, what is meant by data set incompleteness will next be defined and described, followed by a description of methods and systems in accordance with the invention.

Figure 2A:
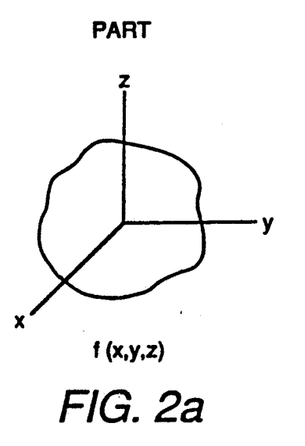
FIGS. 2a, 2b, 2c, 2d, 2e and 2f are diagrams depicting the Rahn transform approach to 3D CT imaging.
Figure 2B:
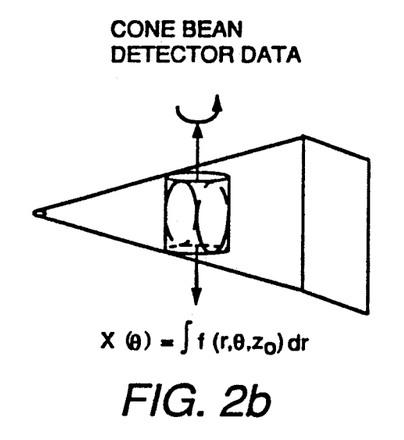
Figure 2C:
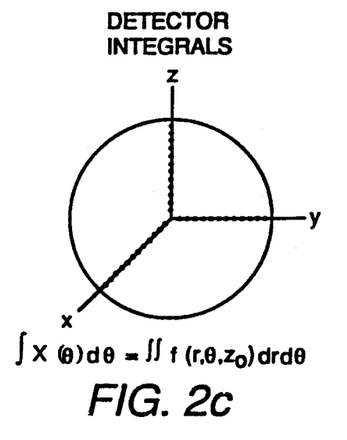
Figure 2D:
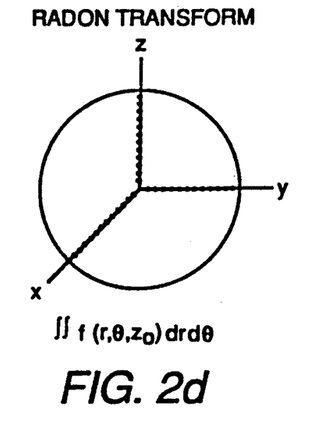
Figure 2E:
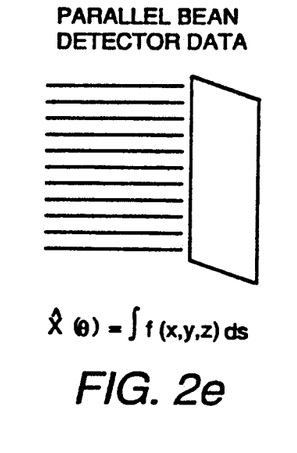
Figure 2F:
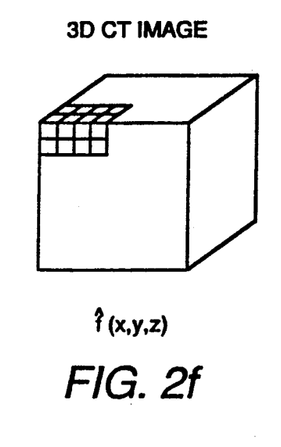

Data set completeness can be defined most clearly and rigorously in terms of the Radon transform approach to 3D imaging, represented in FIGS. 2a through 2f. The object itself is defined in terms of its x-ray attenuation coefficient $f(x,y,z)$ (FIG. 2a). The measured cone beam projection data then corresponds to a line integral of this function over the radial direction $X(\theta) = \int f(r,\theta,z_0)dr$ (FIG. 2b). The line integrals in the parallel of the detector data (also known as detector integrals) are given by $\int X(\theta)d\theta = \int\int f(r,\theta, z_0)dr\, d\theta$ (FIG. 2c). beam case, these detector integrals are simply equal to the Radon transform of the object. In the cone beam case, however, the Radon transform is given instead by $\int\int f(r,\theta,z_0) r\, dr\, d\theta$ (FIG. 2d). The additional factor of r in the Radon transform integral results from the Jacobian of the coordinate transformation from Cartesian to polar coordinates. As depicted in FIGS. 2e and 2f, an inverse Radon transform procedure reconstructs a 3D CT image from the detector integrals. Since direct inverse Radon transformation requires planar integrals of the object as input, an intermediate step of converting cone beam detector integrals to planar integrals may be employed, although a variety of reconstruction techniques are available, as is apparent from the literature.

It is significant to note that the data set is complete if it provides data at every point in Radon transform space; i.e., Radon space is filled with data over the region of support corresponding to the field of view in real space within which the object of interest fits. Therefore, the filling of Radon space by various scanning configuration is of significant interest. (In addition, it can be shown that if detector integral space is filled over the region of support for the object, the data set is complete.)

Figure 3:
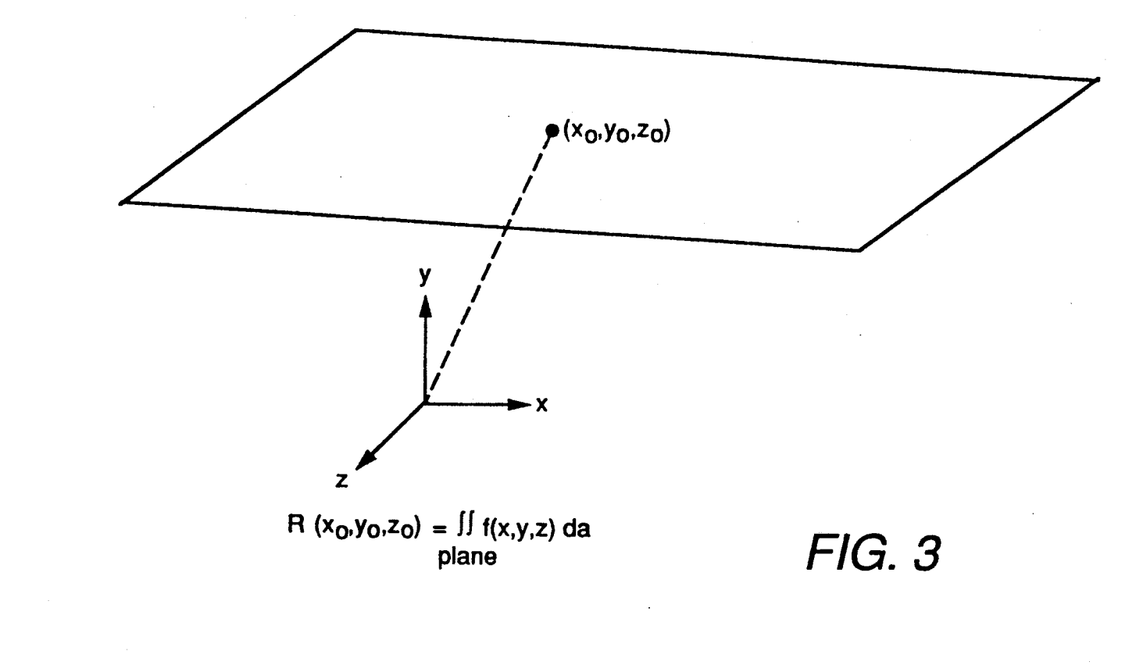
FIG. 3 is a reprentation of the 3D Radon transform of an object at a given point.

As depicted in FIG. 3, the Radon transform of an object at a point $X_o, y_o, Z_o$ is given by the area integral of the x-ray attenuation coefficient over the plane passing through $X_o, y_o, Z_o$ that is perpendicular to the line from the origin to $X_o, y_o, Z_o$, and can be expressed as $$R(x_0, y_0, z_0) = \iint_{plane} f(x,y,z)da$$

In 2D, the situation is similar, except that the integral is over a line, not over a plane.

Any scanning and data acquisition configuration provides data over some volume of Radon space. Described next with reference to FIGS. 4a through 7b are regions in Radon space which are filled and which are not for various 2D and 3D scanning configurations.

Figure 4A:
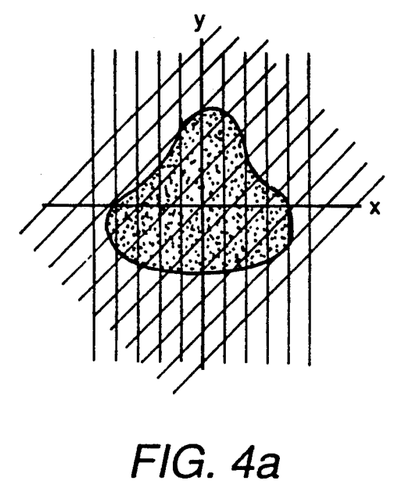
FIGS. 4a and 4b depict Radon space filling in the case of 2D parallel beam CT.
Figure 4B:
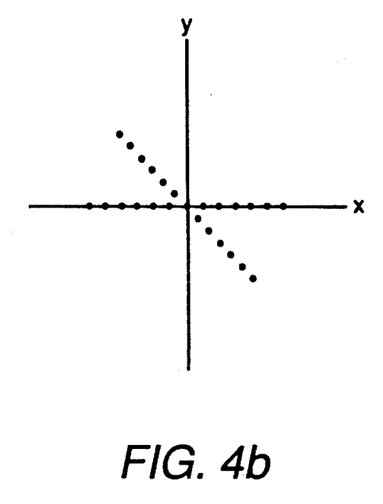
Figure 5A:
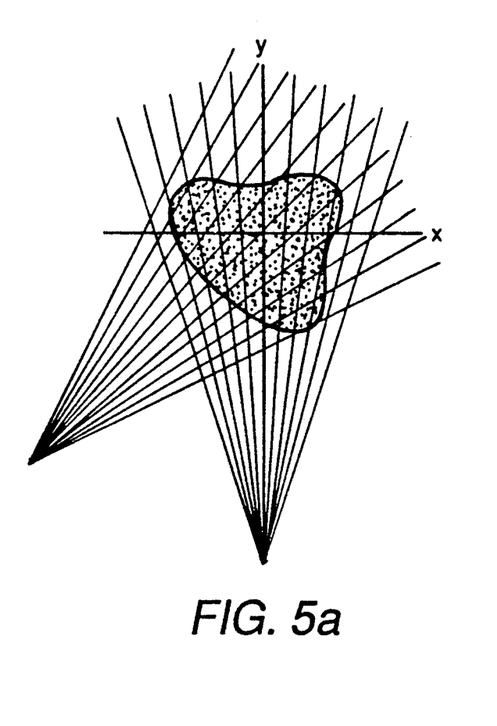
FIGS. 5a and 5b depict Radon space filling in the case of 2D fan beam CT.
Figure 5B:
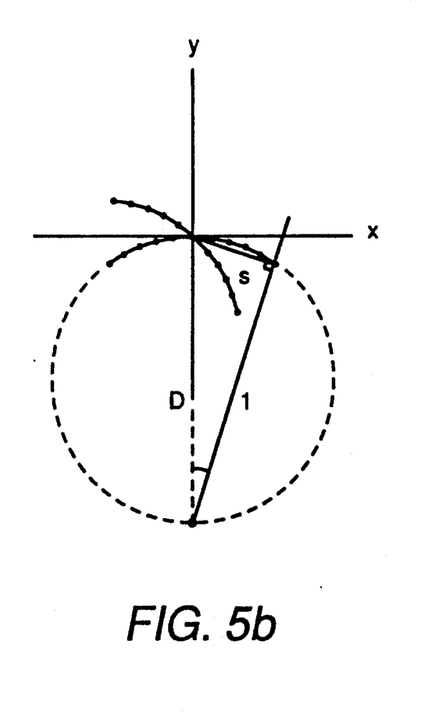

FIGS. 4a and 4b represent Radon space filling for 2D parallel beam CT. The x-ray paths for two view angles are shown in FIG. 4a, and the resulting points in Radon space are shown in FIG. 4b. For each point in Radon space, a line is extended from the origin to the point of interest, and the x-ray intensity is integrated over a line passing through that point and perpendicular to the line to that point from the origin. Such points are shown in FIG. 4b for each ray depicted in FIG. 4a, for each of two view angles.

The situation for fan beam data acquisition is similar (FIGS. 5a and 5b), but here the ray paths diverge from the x-ray source, and the geometry is slightly more complicated. The procedure is the same, however. By way of example, the extreme right-hand ray of the fan beam is analyzed in FIG. 5b. The perpendicular line to the ray is labeled "s". It may be noted that the point of Radon space of interest forms a right triangle with the origin and the x-ray source point. (It is the same point that would be determined in parallel beam geometry for a view angle orientation of one-half the fan angle.) This is generally true for any point in Radon space acquired with the detector in this position. Therefore, by geometry, the points in Radon space lie on the arc of a circle whose diameter is the source to center of rotation distance. Similar arcs are constructed for each view angle position around the object. It can be appreciated from this construct that complete data is provided by rotating source and detector around the object through an angle of 180° plus the fan angle.

Figure 6A:
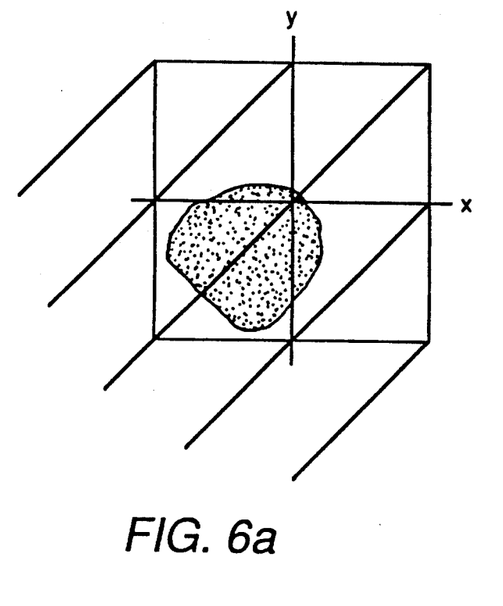
FIGS. 6a and 6b epict Radon space filling in the case of 3D parallel beam CT.
Figure 6B:
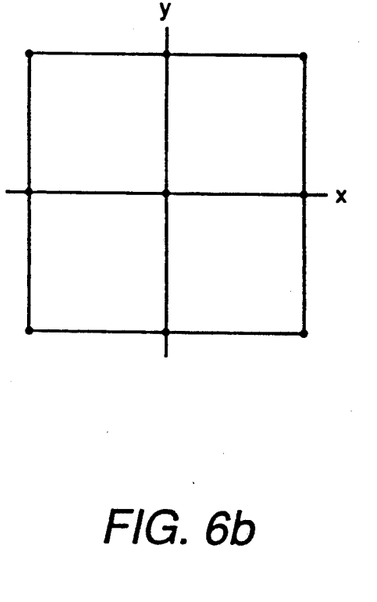

The parallel beam case for 3D is represented in FIGS. 6a and 6b. Here, the x-ray attenuation measurement corresponds to integration in the z direction, and line integrals of the detector data are taken at other orientations in the detector plane to fill in Radon space on a single plane passing through the object. For example, the point in Radon space at $x=0, y=y_o$ corresponds to the detector integral over points in the detector a distance $y_o$ above the x,z plane. Points off axis in Radon space correspond to detector integrals along straight lines with various slopes in detector space. For example, the point at $x=c, y=c$ in Radon space corresponds to detector integrals along lines with slope $-45°$ with respect to the x axis and a distance $\sqrt{2}c$ from the origin.

Figure 7A:
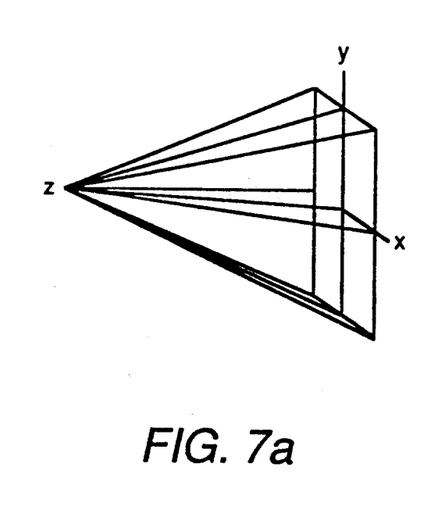
FIGS. 7a and 7b depict Radon space filling in the case of 3D cone beam CT.
Figure 7B:
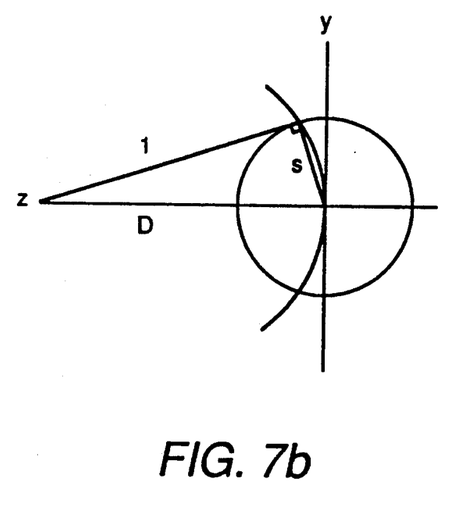
Figure 8:
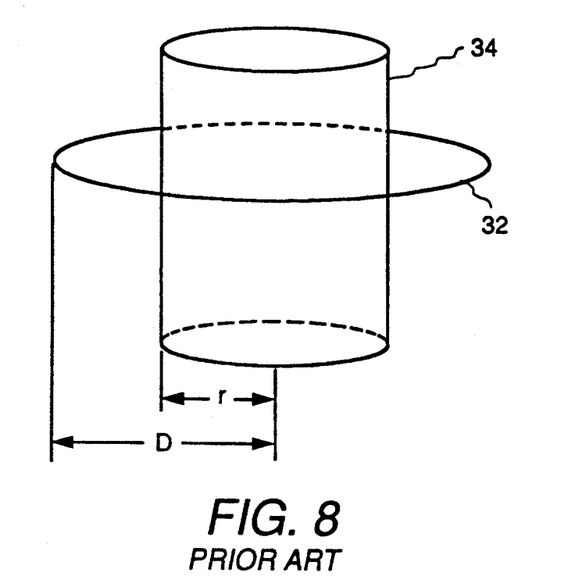
FIG. 8 depicts a prior art circular scanning trajectory corresponding to FIG. 1.
Figure 9:
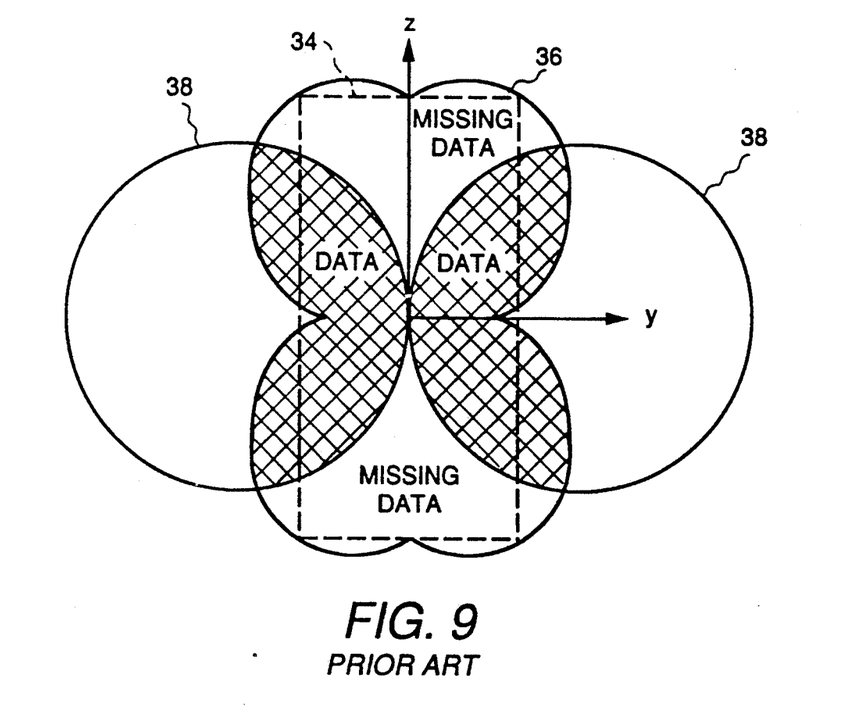
FIG. 9 depicts regions of available data and missing data in Radon space when the prior art scanning configuration of FIGS. 1 and 8 is employed.

The particularly relevant cone beam case in 3D is similarly represented in FIGS. 7a and 7b. Corresponding to FIGS. 7a and 7b are prior art FIG. 1, described hereinabove; prior art FIG. 8, which depicts a single circular source scanning trajectory 32 around a cylindrical field of view 34 within which an object to be scanned fits; and prior art FIG. 9, which depicts in cross-section the intersection of a volume 36 in Radon space comprising the region of support for the field of view 34 with a toric volume 38 representing the region in Radon space for which data are available. In FIG. 9, the diameter of each side of the toric volume 38 is equal to the source to axis of rotation distance D. For purposes of comparison with the Radon space region of support volume 36, superimposed in phantom in FIG. 9 is the real space field of view 34.

In FIGS. 7a and 7b, the exemplary point shown in Radon space corresponds to the detector integral along the top line of the detector data. The geometry is similar to the fan beam case in 2D. The points in Radon space for all detector line integrals at a single view angle correspond to a section of a sphere with diameter equal to the source to center of rotation distance. A new spherical shell of data is created at each view angle, and for a 360° scan, the available data falls inside the toric volume 38 (FIG. 9).

Thus, as represented in FIG. 9, in Radon space data for reconstruction are available at those points within the region of support volume 36 where the region of support volume 36 intersects the toric volume 38, as indicated by the word "data". As indicated by the words "missing data", data are absent for points on the top and bottom of the Radon space region of support volume 36 because these points correspond to planes parallel and near parallel to the x,y plane and data for these planes are not available because of the cone beam nature of the x-ray source. The region of missing data narrows as z approaches the midplane, and for $z=0$ (on the midplane), all the required data are available.

As shown by Smith, 1985, above, a cone beam data set is complete if there is a point from the x-ray source scanning trajectory on each plane passing through the object of interest. (The detector is assumed to be locked in position relative to the source and large enough to span the object under inspection.) Relating this to FIG. 8 where the circular source scanning trajectory 32 surrounds the exemplary field of view 34, by Smith's criterion the trajectory 32 is incomplete because a number of horizontal and near-horizontal planes pass through the region of support of the object (i.e. the field of view 34) without intersecting the source scanning trajectory 32. These planes are exactly those that correspond to the missing data in Radon space in FIG. 9. When applying Smith's criterion, it may be noted that, for large z, the number of planes through the object not intersecting the source scanning trajectory is relatively large, and the number decreases as z decreases. This same behavior is noted in Radon space, as shown in FIG. 9. It may also be noted that vertical planes passing through the object do intersect the scanning trajectory, and that, as the diameter of the trajectory increases relative to the diameter of the object, the amount of missing data (the number of planes that do not intersect the scanning trajectory) decreases.

Figure 10:
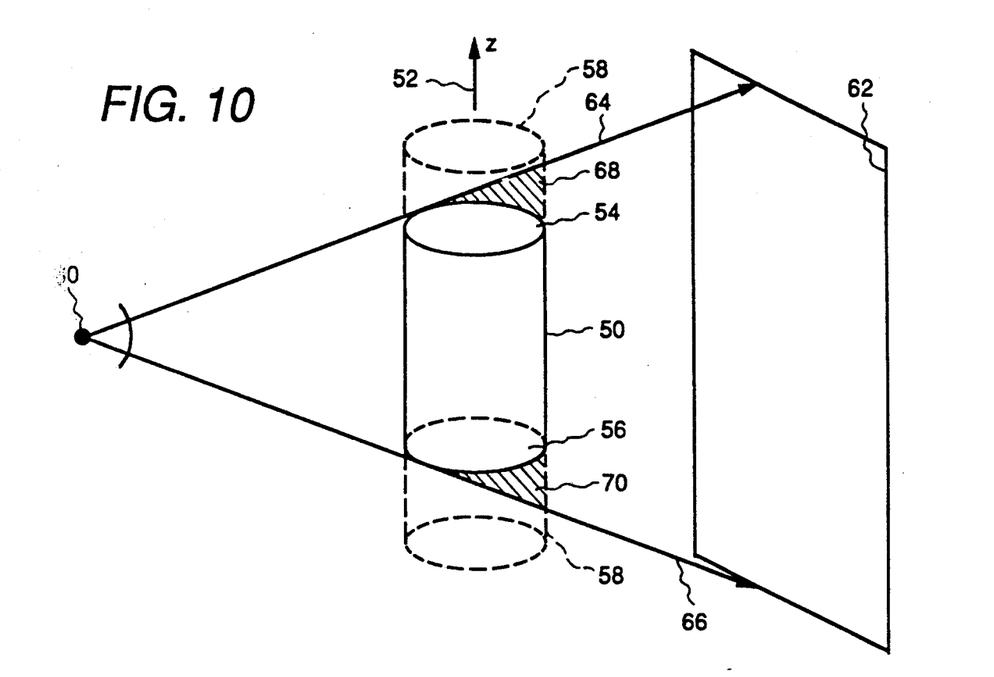
FIG. 10 depicts a configuration wherein an x-ray source and a two-dimensional area detector scan a cylindrical field of view which is a subsection of a larger cylindrical object wherein measured projections are corrupted by contributions from sections of the object outside the field of view.

Considering now in particular the problem of data corruption by overlying material in the situation where an object to be imaged is of greater axial extent than a field of view, in FIG. 10, depicted is a cylindrical field of view 50 radially centered on a z-axis or rotation axis 52, and having an axial extent defined by two endplanes 54 and 56 perpendicular to the rotation axis 52. An object 58 to be imaged is of greater axial extent that the field of view 50. Thus, only that portion of the object 58 lying within the field of view 50 is to be imaged. In FIG. 10, an x-ray source 60 and a two-dimensional detector 62 are scanning the field of view 50. The extreme rays 64 and 66 are required to acquire data over the entire field of view 50 of interest, it can be seen that rays near the ends of the cylindrical field of view 50 penetrate through portions 68 and 70 of the object 58 outside the field of view 50. This overlying material 68 and 70 then corrupts the projections acquired by the area detector 62 which projections, in the reconstruction algorithm, are assumed to contain contributions from the field of view 50 only. A reconstructed image therefore contains contributions from regions outside the field of view, and artifacts result.

Figure 11:
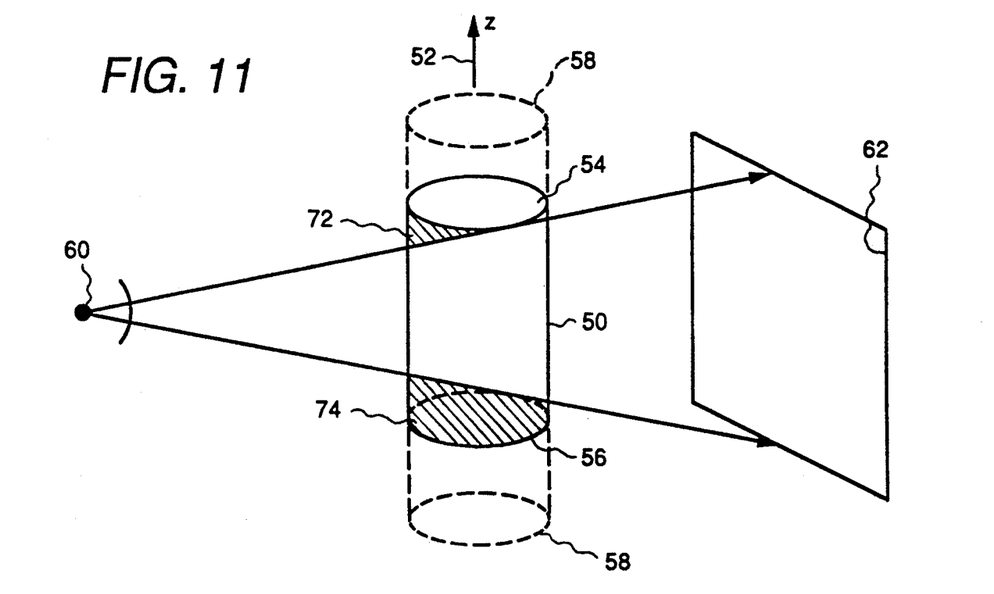
FIG. 11 depicts a similar configuration, wherein data is acquired over a subset of the cylindrical field of view.

One approach to the problem of data corruption due to overlying material is depicted in FIG. 11, which is comparable to FIG. 10 except that the x-ray cone angle is reduced so that data is acquired only over a subset of the cylindrical field of view 50. However, this configuration results in a significant loss of data, since regions 72 and 74 just inside the ends of the cylindrical field of view 50 are not sampled by projection data at all. This result exacerbates the missing data problem which is already present in 3D CT image reconstruction as described hereinabove.

It may be noted that approaches intermediate those of FIGS. 10 and 11 are known in the prior art. For example, Feldkamp et al., 1984, above, describe a reconstruction technique which corresponds to a scanning configuration wherein the outer rays of the x-ray cone beam pass through the field of view at the rotation axis.

Figure 12:
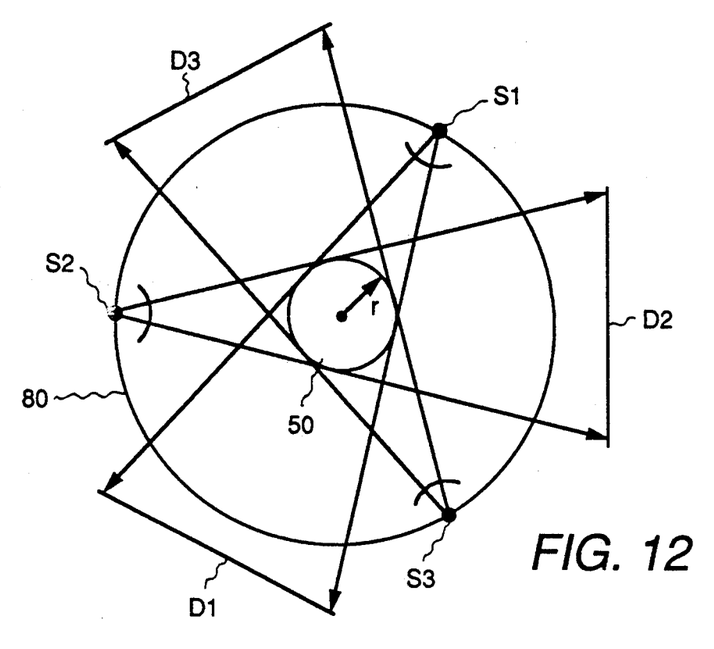
FIG. 12 is a top view of a system embodying the scanning configuration of the invention.
Figure 13:
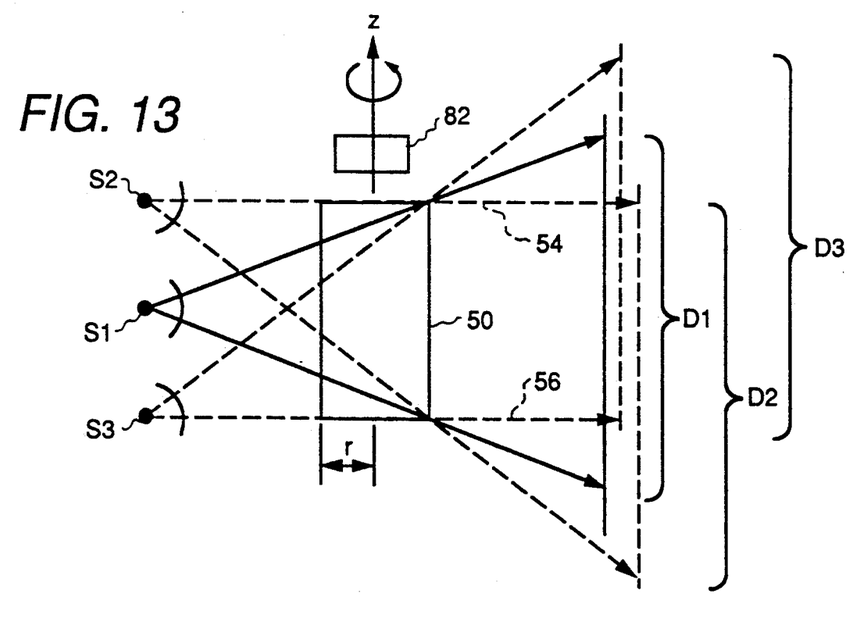
FIG. 13 is a side view of a system embodying the scanning configuration of the invention, modified for purposes of illustration to better represent the vertical offset between the several circular scanning trajectories.

FIGS. 12 and 13 depict a scanning configuration in accordance with the invention. In particular, FIG. 12 is a top view, while FIG. 13 is a side view modified for purposes of illustration by repositioning the x-ray source so as to more clearly depict the vertical offset. In the top view of FIG. 12, the various circular source scanning trajectories are superimposed and lie on a single circle 80. The cylindrical field of view 50 is defined by a radius r, and has an axial extent between the two endplane 54

Corresponding to the configuration of FIG. 11, above, an x-ray source S1 scans along a circular scanning trajectory centered on the rotation axis and lying in a plane intermediate the two endplanes 54. Corresponding to the source S1 is a detector D1, which is sized to acquire cone beam projection data from rays passing through the field of view 50, but not from rays outside the field of view.

In accordance with the invention, two further circular source scanning trajectories are defined lying in the endplanes 54 and 56, along which sources S2 and S3 scan. Detectors D2 and D3 correspond to the source S2 and S3. Scanning effected by source S2 and its corresponding detector D2 does an excellent job of filling a missing data at the top of the cylindrical field of view 50, while scanning by the source S3 and detector D3 does an excellent job of filling in missing data at the bottom of the cylindrical field of view 50. All of the scans acquire data only over projection paths completely included in the cylindrical field of view 50.

It will be appreciated that each of the detectors D1, D2 and D3 is fixed in position relative to its corresponding source S1, S2 and S3. Each of the sources S1, S2 and S3 and its corresponding detector D1, D2 and D3 may be viewed as a scan head. Scanning is accomplished in a conventional manner by moving the sources along the respective scanning circles relative to the object an the field of view 50. Since it is relative movement which effects scanning, either the object and with it the field of view 50 can be rotated while the sources and detectors remain stationary, or the object and field of view 50 can remain stationary while the sources and detector move. By way of example, in FIG. 13 a generalized scanning element 82 is connected to the object in order to move the object as required, while the sources and detectors remain stationary.

As may be seen particularly in FIG. 12, in order to reduce interference of X-rays from one source interacting with the detector corresponding to another source, the sources are angularly offset. In the particular configuration shown, the angular offset is 120°. Other angular offsets may be employed, chosen for purposes of scatter reduction, mechanical convenience, or other system considerations.

It will be appreciated that the various scans at different locations need not be made simultaneously. Simultaneous scanning may be required in medical applications to reduce or eliminate motion artifacts, but are less necessary in industrial applications where a part to be inspected can be securely fixtured into position. Thus, it will be appreciated that one scan head comprising a single x-ray source and a single detector may be repositioned to effect scanning allowing each of the scanning circles, or a plurality of scan heads may be employed. Where only a single scan head is employed, a preferred scanning element 82 is a two-axis CNC part manipulator, the two axes being a vertical translation axis and a rotation axis.

It will further be appreciated that scanning along various numbers of circular source scanning trajectories can be done in accordance with the invention. Scanning along the two circular source scanning trajectories lying in the end-planes 54 and 56, that is with sources S2 and S3 and corresponding detectors D2 and D3, reduces hardware costs and complexity, but requires image reconstruction with less available data. Scanning along three trajectories as depicted is particularly attractive, because scan 1 provides exact data on the midplane at the center of the field of view 50, while scans 2 and 3 provide exact data on midplanes at the top and bottom of the object field of view. Scanning along four or more source trajectories (simultaneously) increases hardware costs and complexity, but reduces the missing data even more and, perhaps more importantly, allows selection of the position of the midplane locations where the reconstruction is exact.

Figure 14:
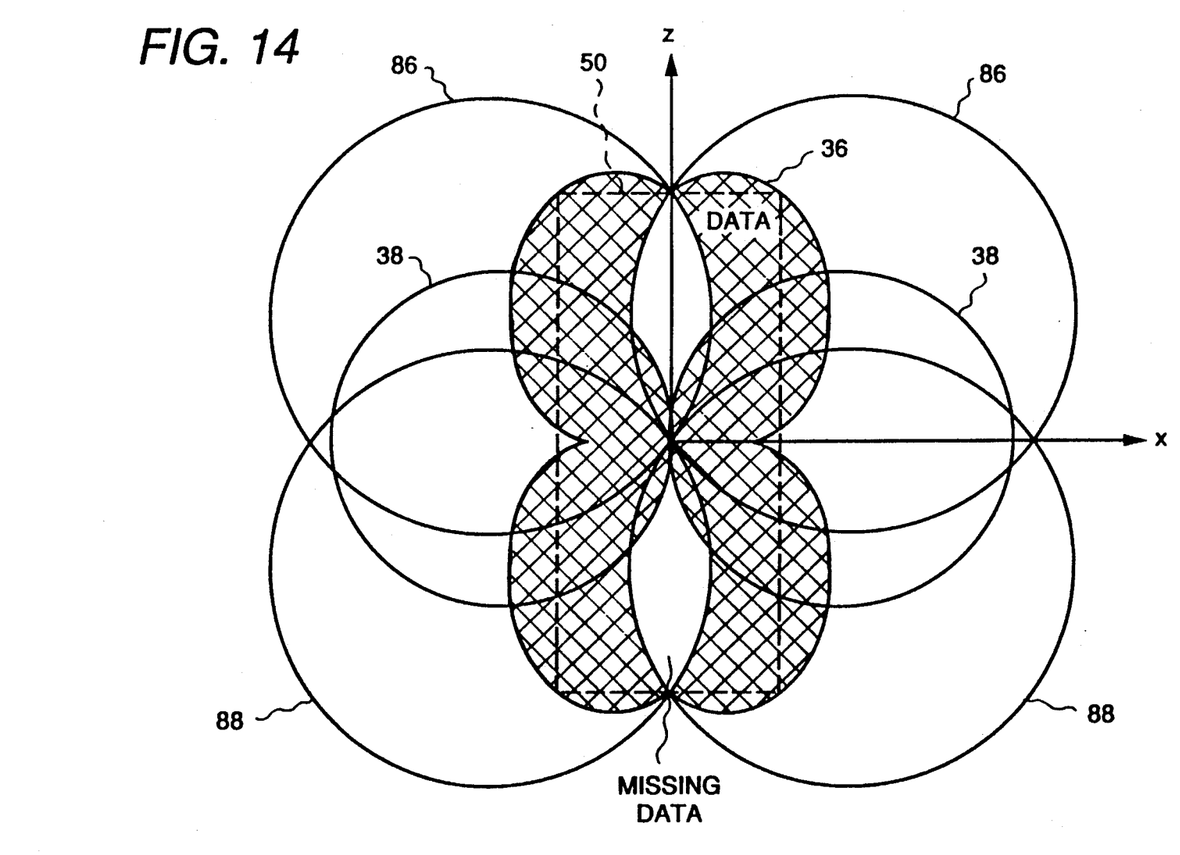
FIG. 14 depicts regions of available data and missing data in Radon space when the scanning configuration of FIGS. 12 and 13 is employed.

FIG. 14 depicts Radon space filling as is achieved with the illustrated embodiment wherein scanning is along three circular source scanning trajectories. FIG. 14 depicts in cross-section the Radon space region of support 36 corresponding to a cylindrical field of view, as in FIG. 9. Superimposed in FIG. 14 are three available data circles respectively defining additional toric volumes 86 and 88 corresponding to the scans of sources S2 and S3 along the trajectories lying within the endplanes 54 and 56. Again, available data and missing data areas are indicated.

In FIG. 14, it may be noted that the Radon space region 36 which must be filled for the cylindrical field of view dips down at the poles, just as do the regions of available data. Thus, the shapes of the available data and the region of support are well matched for a cylindrical field of view.

While the invention is described and claimed herein in terms of acquiring data only from rays passing through the field of view, it will be appreciated that the detectors may, as an incidental matter, acquire data from rays passing through regions outside the field of view. However, this particular data is discarded at some point and not employed for reconstruction. The particular point where the data is discarded is arbitrary. Preferably the ar detectors are optimally sized to match the field of view and the source scanning geometry so that no detector area is "wasted". However, in practical systems, it is not always possible to optimally size the area detectors. Accordingly, the terminology employed herein with reference to acquiring data only from rays passing through the field of view is intended to be given a reasonable interpretation, and does not preclude incidentally requiring data outside the field of view, which data is subsequently discarded.

While specific embodiments of the invention have been illustrated and described herein, it is realized that modifications and changes will occur to those skilled in the art. It is therefore to be understood that the appended claims are intended to cover all such modifications and changes as fall within the true spirit and scope of the invention.

What is claimed is:

1. A scanning and data acquisition method for three-dimensional computerized tomography (CT) imaging of a portion of an object within a cylindrical field of view radially centered on a rotation axis and having an axial extent defined by two endplanes perpendicular to the rotation axis, the object being of greater axial extent than the field of view, said method comprising;
    defining at least two circular source scanning trajectories centered on the rotation axis and lying respectively in the two endplanes; and
    employing at least one cone beam x-ray source and at least one corresponding two-dimensional array detector positioned with reference to the source and with reference to the field of view to scan the object at a plurality of relative angular positions along the source scanning trajectories to acquire cone beam projection data, while acquiring data only from rays passing through the field of view.

2. A method in accordance with claim 1, which further comprises:
    defining at last one additional circular source scanning trajectory centered on the rotation axis and lying in a plane intermediate the two endplanes; and
    scanning the object at a plurality of angular positions along the additional source scanning trajectory to acquire cone beam projection data from rays passing through the field of view.

3. A method in accordance with claim 2, which comprises:

providing a separate scan head corresponding to each of the source scanning trajectories, each of the scan heads including a cone beam x-ray source and a two-dimensional array detector positioned with reference to the x-ray source of the particular scan head and the field of view for reobtaining cone beam projection data; and employing the scan heads to simultaneously scan the object along the source scanning trajectories.

4. A method in accordance with claim 2, which comprises locating the additional source scanning trajectory in a plane where it is desired to obtain exact two-dimensional computerized tomography data.

5. A method in accordance with claim 1, which comprises:

providing at least two scan heads corresponding to the two source scanning trajectories, each scan head including a cone beam x-ray source and a two-dimensional array detector positioned with reference to the X-ray source of the particular scan head and the field of view for obtaining cone beam projection data; and employing the two scan heads to simultaneously scan the object along the two source scanning trajectories.

6. A scanning and data acquisition system for three-dimensional computerized tomography (CT) imaging of a portion of an object within a cylindrical field of view radially centered on a rotation axis and having an axial extent defined by two endplanes perpendicular to the rotation axis, the object being of greater axial extent that the field of view, said system comprising:

at least one cone beam x-ray source;

at least one two-dimensional array detector corresponding to said source and positioned with reference to said source and the field of view for obtaining cone beam projection data from rays passing through the field of view; and a scanning element for effecting relative motion between said at least one source and the object, said source moving relative to the object along at least two circular source scanning trajectories centered on the rotation axis and lying respectively in the two endplanes, so as to acquire cone beam projection data only from rays passing through the field of view with said source at a plurality of angular positions on the scanning trajectories.

7. A system in accordance with claim 6, wherein said scanning element effects relative motion between said at least one source and the object along an additional circular source scanning trajectory centered on the rotation axis and lying in a plane intermediate the two endplanes.

8. A scanning and data acquisition system for three-dimensional computerized tomography (CT) imaging of a portion of an object within a cylindrical field of view radially centered on a rotation axis and having an axial extent defined by two endplanes perpendicular to the rotation axis, the object being of greater axial extent than the field of view, said system comprising:

a pair of cone beam x-ray sources;

a pair of two-dimensional array detectors respectively corresponding to said sources and positioned with reference to said sources and the field of view for obtaining cone beam projection data from x-rays passing through the field of view; and a scanning element for effecting relative motion between said sources and the object, said sources moving relative to the object along a corresponding pair of circular source scanning trajectories centered on the rotation axis and lying respectively in the two endplanes, so as to acquire cone beam projection data only from rays passing through the field of view with said sources at a plurality of angular positions on the scanning trajectories.

9. A system in accordance with claim 8, which further comprises:

at least one additional cone beam x-ray source; and at least one additional two-dimensional array detector corresponding to said additional source and positioned with reference to said additional source for obtaining cone beam projection data from rays passing through the field of view; and wherein said scanning element effects relative motion between said additional source and the object, said additional source moving relative to the object along an additional circular source scanning trajectory centered on the rotation axis and lying in a plane intermediate the two endplanes.

10. A system in accordance with claim 8, wherein said cone beam x-ray sources are angularly offset so as to reduce interference caused by x-rays from one source interacting with the detector corresponding to the other source.

11. A system in accordance with claim 9, wherein said cone beam x-ray sources are angularly offset so as to reduce interference caused by x-rays from one source interacting with the detector corresponding to another source.

* * * * *